United States Patent [19]

Kerfoot, Jr.

[11] E Patent Number: Re. 31,965

[45] Reissued Date of Patent: Aug. 6, 1985

[54] COMPLIANTLY MOUNTABLE TURBINE CARTRIDGE ASSEMBLY FOR GAS-DRIVEN DENTAL HANDPIECE

[75] Inventor: Frank W. Kerfoot, Jr., Newtown Square, Pa.

[73] Assignee: Syntex (U.S.A.) Inc., Palo Alto, Calif.

[21] Appl. No.: 317,698

[22] Filed: Nov. 2, 1981

Related U.S. Patent Documents

Reissue of:

[64] Patent No.: 4,249,896
Issued: Feb. 10, 1981
Appl. No.: 947,215
Filed: Sep. 29, 1978

[51] Int. Cl.[3] ..... A61C 1/05

[52] U.S. Cl. ..... 433/132; 433/126

[58] Field of Search ..... 433/126, 132, 133

[56] References Cited

U.S. PATENT DOCUMENTS

| | | | |
|---|---|---|---|
| 2,945,299 | 7/1960 | Fritz | 433/132 |
| 3,092,908 | 6/1963 | Flatland | 433/132 |
| 3,218,028 | 11/1965 | Borden | 415/503 |
| 3,325,899 | 6/1967 | Staunt | 433/132 |
| 3,380,162 | 4/1968 | Heathe | 433/132 |
| 3,381,387 | 5/1968 | Lawrence et al. | 433/132 |
| 3,888,008 | 6/1975 | Lake et al. | 433/132 |
| 4,071,954 | 2/1978 | Eibofner | 433/132 |

*Primary Examiner*—Robert Peshock
*Attorney, Agent, or Firm*—David A. Lowin; John A. Dhuey

[57] ABSTRACT

A single-unit turbine cartridge assembly for a gas-driven dental handpiece includes a pair of bearing assemblies mounted on a turbine rotor shaft and a ring of resilient material around each bearing assembly. The resilient ring provides radial support for the turbine cartridge assembly within the housing of the handpiece and substantially dampens the transfer of vibration from the cartridge assembly to the handpiece during use of the handpiece. The turbine cartridge assembly may optionally include bearing axial pre-load means in association with one or more of the bearing assemblies. The turbine cartridge assembly also includes means for retaining the resilient radial support means and the bearing axial preload means, when used, in association with the bearing assemblies, so as to permit removal, and reinstallation, of the cartridge assembly as an entire unit from, and to, the housing in the dental handpiece.

67 Claims, 7 Drawing Figures

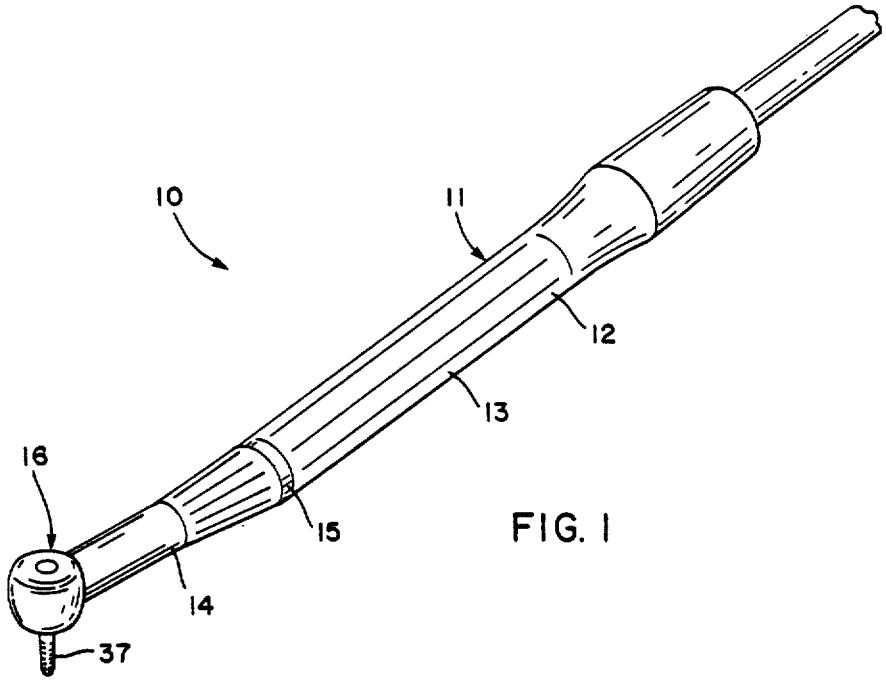
FIG. 1
FIG. 2
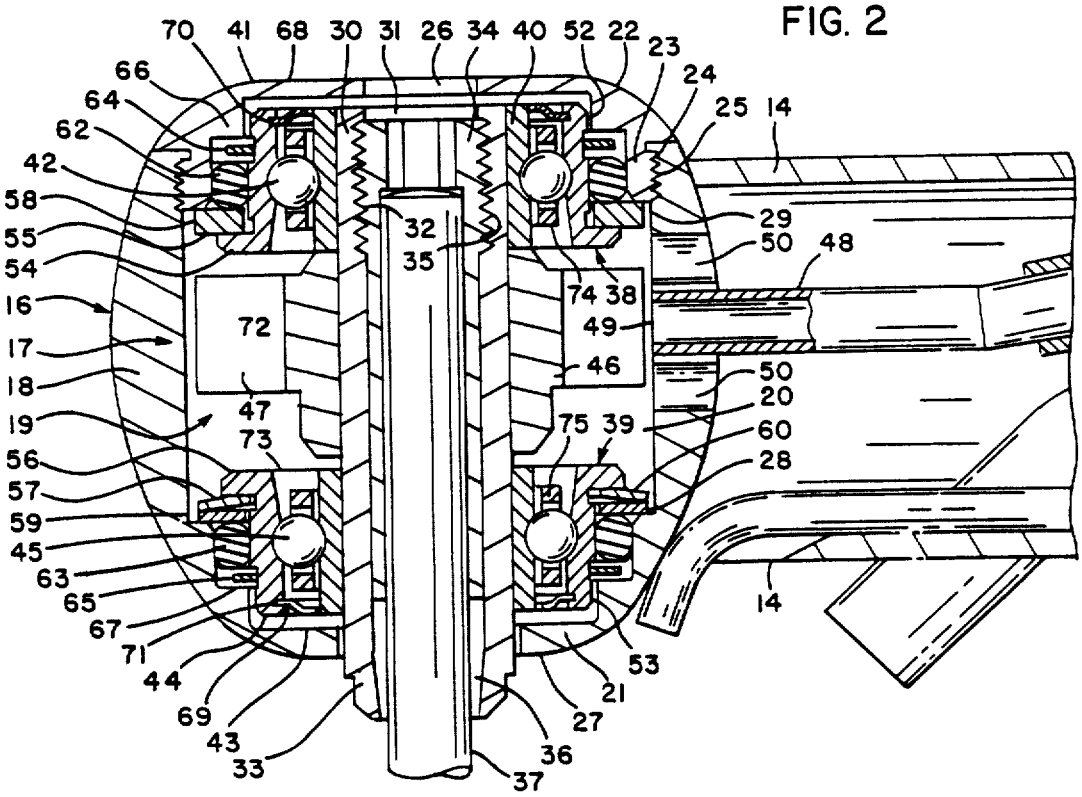

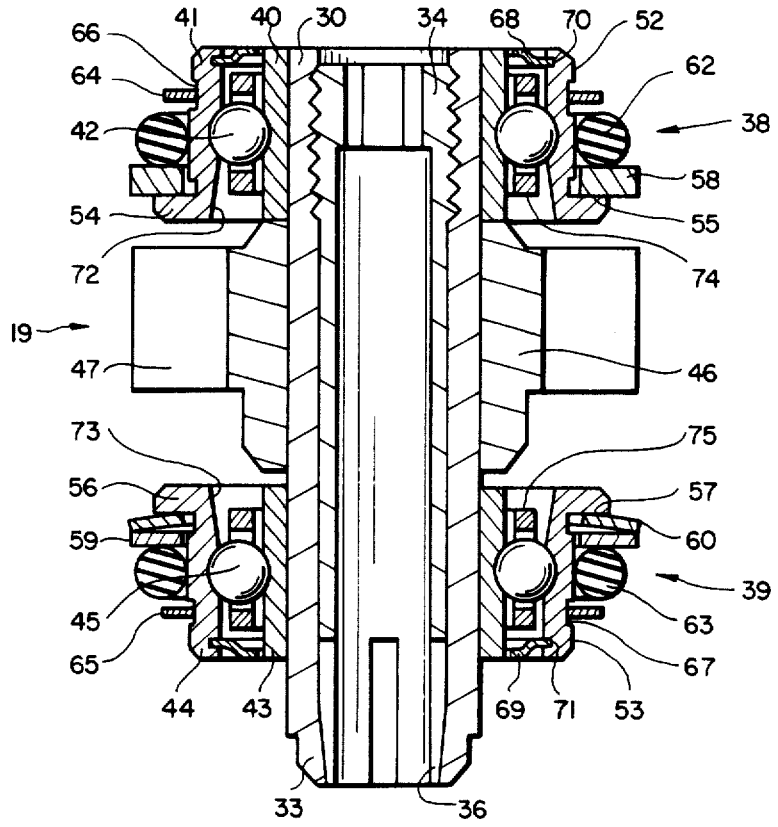
FIG__3
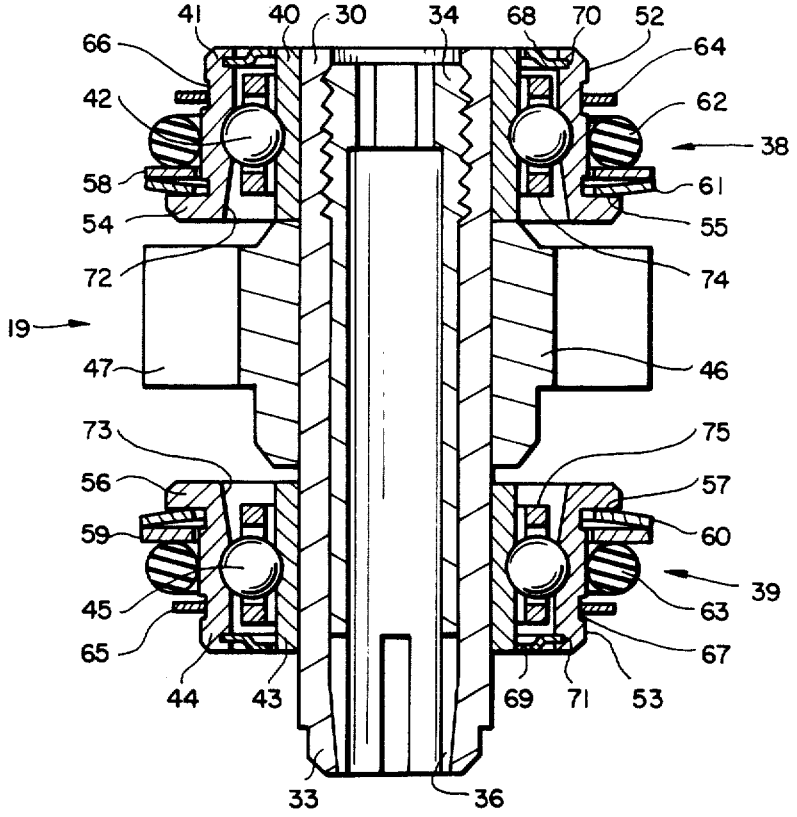
FIG__4

COMPLIANTLY MOUNTABLE TURBINE CARTRIDGE ASSEMBLY FOR GAS-DRIVEN DENTAL HANDPIECE

Matter enclosed in heavy brackets [ ] appears in the original patent but forms no part of this reissue specification; matter printed in italics indicates the additions made by reissue.

BACKGROUND OF THE INVENTION

1. Field

Dental handpieces having gas-driven motors are well known. Of particular interest herein is a high-speed gas-driven dental handpiece having decreased noise and improved vibration damping characteristics.

2. State of the Art

A dental handpiece of a type having a high-speed gas-driven motor, of which the turbine rotor and bearings are replaceable as a multi-piece unit within the motor housing, is described in U.S. Pat. No. 3,074,167 to Turchi et al. A rotor of a high-speed motor of this type will rotate at speeds of 250,000 to 400,000 rpm, or more, during use of the handpiece by a dentist. Significant amounts of vibration and noise may be transmitted from the motor to the handle portion during use of a high-speed handpiece having a rotor bearing cage in direct contact with the handpiece motor housing, such as shown in the Turchi et al U.S. Pat. No. 3,074,167 patent. Vibration and noise even in small amounts can be quite disturbing to dentist and patient alike, and may be especially disturbing when, at certain critical rotor operating speeds, resonance effects greatly enhance or amplify the noise or vibration originating from the gas-driven motor.

A high-speed handpiece having reduced vibration and noise transmitting characteristics is disclosed in U.S. Pat. No. 3,499,223 to Lieb et al, wherein vibration damping rings fabricated of non-metallic or rubbery materials are interposed between the metallic rotor bearings and a metallic motor housing. These vibration damping rings are described as insertable within a gas-driven motor housing separately from the turbine rotor-and-bearing assembly. A disadvantage of this arrangement is that during removal and reinstallation of a turbine assembly by a handpiece user in a dental office one or both of the vibration damping rings may frequently become lodged in the motor housing, with resultant difficulty following in the removal of the ring. Also, reinstallation of each ring separately from the turbine-and-bearing assembly is a time-consuming chore requiring a relatively high degree of care to avoid improper orientation or seating of the ring in the motor housing.

Another problem associated with proper installation or positioning of a turbine-and-bearing assembly within a gas-driven motor housing is in obtaining proper rotor alignment and static pre-loading of the bearings within the housing. One aspect of proper rotor alignment is the degree of concentricity maintained between the motor housing axis and the axis of rotation of a dental bur which is mounted by its shank within the turbine cartridge assembly rotor shaft. The degree of concentricity is, in turn, related to bur run-out, that is, the distance of movement of a rotating bur from its theoretical axis as measured in a plane perpendicular to the rotor shaft axis, the plane intersecting the tip of the bur. Typically, a dental bur has some imbalance as a result of manufacture or because of an irregular configuration of the bur work surface. The combination of poor concentricity and bur imbalance may provide a considerable amount of vibration during use of the handpiece especially at or near the critical frequency of rotation of the turbine.

Improper axial or radial alignment of the rotor shaft with respect to the motor housing, or the application of too little or too much static pre-loading to the rotor shaft bearings, may also lead to excessive noise and vibration causing pre-mature wear and failure of the bearings. The problem of misalignment may be especially acute with a handpiece having separately-installed vibration damping rings, or spring-like bearing pre-loading elements, or both, where special care must be taken to prevent distortion of the rings, misalignment of the rotor, improper static pre-loading of the bearings, or loss of the various separately-installed components.

There is need, therefore, for a high-speed gas-driven dental handpiece having a turbine-and-bearing assembly which can be easily removed and reinstalled in a motor housing as a unitary assembly which contains all of the various parts for achieving proper radial and axial alignment to provide a high degree of concentricity, and which turbine cartridge assembly when installed in a handpiece motor housing may provide a proper degree of static preloading to the rotor shaft bearings.

SUMMARY OF THE INVENTION

A turbine-and-bearing assembly for a high speed gas-driven motor of a dental handpiece of the present invention provides an advantage of improved ease of removal and reinstallation of the turbine assembly from a motor housing as a unitary assembly. Secondly, the turbine assembly of this invention is easily alignable within a motor housing in a manner that provides a proper degree of pre-loading force to the rotor shaft bearings for minimum wear of the bearings. The turbine assembly of this invention when installed in a high-speed dental handpiece provides low transmission of vibration from the motor housing to the handle portion of the handpiece and reduced bur run-out.

These and other advantages are provided by a turbine cartridge assembly which is removably positionable as a unit within a housing of a gas-driven motor of a dental handpiece. The motor housing is typically located in one end portion of a dental handpiece and is defined by a substantially cylindrical side wall and a pair of oppositely disposed end walls transverse to the side wall, with means for supporting a turbine cartridge assembly located on portions of the side wall and end walls. The turbine cartridge assembly may in one embodiment comprise a rotor shaft having a plurality of vanes thereon, the rotor shaft having an axis of rotation substantially coincident with the axis of the cylindrical side wall of the motor housing, a first bearing assembly comprising an inner race fixed to the rotor shaft, an outer race, and a plurality of movable bearing elements frictionally engaged with and confined between the inner race and the outer race, a second bearing assembly comprising an inner race fixed to the rotor shaft in spaced relationship with the inner race of the first bearing assembly, an outer race, and a plurality of movable bearing elements frictionally engaged with and confined between the inner race and the outer race of the second bearing assembly, radial support means associated with each of the first and second bearing assemblies, the radial support means providing radial support for the turbine cartridge assembly when in contact with the substantially cylindrical side wall of the motor housing, rigid axial support means associated with the outer race of the first bearing assembly for axially supporting the first bearing assembly outer race upon turbine cartridge support means located on an end wall portion of the housing, bearing pre-loading means comprising flexible axial support means associated with the outer race of the second bearing assembly for yieldingly supporting the outer race upon turbine cartridge support means located on an end wall portion of the housing to provide a controlled axial force on the outer race of the second bearing assembly, which force is transmitted through the rotor shaft to the first bearing assembly to provide pre-loading to the first bearing assembly, and means for retaining the radial support means and the flexible axial support means upon the outer race of the second bearing assembly. The rigid axial support means and the flexible axial support means coact with the turbine cartridge support means on the housing end wall to provide axial pre-loading of the first and second bearing assemblies when the turbine cartridge assembly is operatively positioned within the motor housing.

The aforementioned rigid axial support means and flexible axial support means comprise means for yieldingly coacting with the turbine cartridge assembly support means in the motor housing of a dental handpiece to provide axial pre-loading of the first and second bearing assemblies when the turbine cartridge assembly is operably positioned within the motor housing. It is an advantage of the invention that various degrees of pre-loading may be provided for a turbine cartridge assembly by the axial pre-load means to compensate for varying degrees of tolerances that exist between components of one bearing assembly and another. Thus bearing assemblies may be employed which have a broader range of component tolerances or "stop" between bearing components thereby providing an advantage in economy of manufacture.

It is another feature of the invention that the entire turbine cartridge assembly is adapted for placement in, and removal from, the housing as a unitary assembly so that during field replacement of the turbine cartridge assembly, the various means for obtaining proper rotor alignment, bearing pre-load or vibration damping are retained on the turbine cartridge assembly and need not be separately removed from, or inserted in, the handpiece motor housing.

The rigid axial support means typically comprises a flange extending radially outwardly from and integrally formed with the outer race of each of the first and second bearing assemblies, although various other constructions affording a rigid flange, or the equivalent thereof, may be provided. The flexible axial support means typically includes at least one resilient spacer member circumferentially disposed about at least one of the bearing assembly outer races. The resilient spacer member, interposed between the turbine cartridge support means located on the motor housing end walls and the rigid axial support means of the outer race of one of the bearing assemblies, is adapted to transmit a controlled compression force therebetween so as to urge the outer race toward the rotor vanes in a direction substantially parallel with the axis of the rotor shaft. It is preferred that the resilient spacer member have a spring constant sufficient to provide a static pre-load to each of the bearing assemblies in the axial direction in the range of about 0.5 to about 1.5 pounds when the turbine cartridge assembly is operably positioned within the motor housing.

The turbine cartridge assembly also includes means for retaining the flexible axial support means and other support components upon the outer race of the second bearing assembly and may also include means for retaining the rigid axial support means and other support components upon the outer race of the first bearing assembly, particularly where the rigid axial support means is not integrally formed with the outer race. Retention of these various support means upon each of the bearing assembly outer races allows removal and reinstallation of all components of the turbine assembly as a unitary cartridge, which thus precludes the loss of the support components during handling of the turbine cartridge assembly.

The turbine cartridge assembly includes radial support means which provide radial support for each of the first and second bearing assemblies against the substantially cylindrical side wall of the housing. In addition to providing proper radial positioning of the turbine cartridge assembly with respect to the motor housing side wall, it is desirable that the radial support means ideally have mechanical properties which inhibit the transmission of vibration from a rotating turbine cartridge assembly to the motor housing. In preferred embodiments of the invention, the radial support means comprises a ring of resilient material interposed between each of the first and second bearing assembly outer walls and a portion of the housing cylindrical side wall adjacent each of the bearing assemblies. These resilient rings are characterized in providing sufficiently rigid radial support of the turbine cartridge assembly while, at the same time, providing means for damping or reducing the transmission of vibration between the turbine bearings and the motor housing.

A dental handpiece having a turbine cartridge assembly of this invention which includes radial support means comprising resilient, vibration-damping rings may be described as compliantly mounted or suspended within the handpiece motor housing.

A significant advantage is provided by a turbine cartridge assembly of this invention including radial support means comprising resilient members having a particular physical characteristic, as hereinafter defined. In some conventional handpieces having metallic or substantially non-resilient supports between the turbine bearings and the motor housing, there may be a very low degree of resilience, as measured by spring rate, of about 5000 pounds per inch. This very high spring rate provides for little damping of vibration between the bearing and the motor housing. In the present invention, resilient elements are utilized between the turbine cartridge bearing assemblies and the motor housing wall, which resilient elements have spring rates of 80 to 100 pounds per inch. This greatly reduced spring rate provides improved damping of vibration which is characteristic of the compliantly mountable turbine cartridge assembly of this invention.

The radial support means of the turbine cartridge assembly of the invention may, however, in a lesser preferred embodiment, comprise substantially non-resilient members such as provided by the metallic outer wall of each of the bearing assembly outer races.

In another embodiment of the invention, the turbine cartridge assembly may comprise a rotor shaft having a plurality of vanes thereon, the rotor shaft defining an axis of rotation, a first bearing assembly comprising an inner race fixed to the rotor shaft, an outer race, and a plurality of movable bearing elements frictionally engaged with the confined between the inner race and the outer race, a second bearing assembly comprising an inner race fixed to the rotor shaft, an outer race, and a plurality of movable bearing elements frictionally engaged with and confined between the inner race and the outer race of the second bearing assembly, radial support means associated with each of the first and second bearing assemblies, the radial support means comprising a resilient member interposed between each of the bearing assemblies and an adjacent portion of the housing side wall, the radial support means providing vibration-damping radial support for the turbine cartridge assembly upon the substantially cylindrical side wall of a handpiece housing, and retaining means mounted on each of the bearing assembly outer races for retaining the radial support means upon the turbine cartridge assembly. Though this embodiment lacks flexible support means or the aforementioned means for yieldingly coacting with the turbine cartridge assembly support means, which provide axial static pre-loading of the bearing assemblies, the inclusion of radial support means having a resilient, vibration-damping nature provides a compliantly mountable or suspendable turbine cartridge assembly for a handpiece housing. Inasmuch as there is a lack of the aforementioned axial pre-load means, the turbine cartridge assembly may require bearing assemblies having component tolerances which provide a limited amount of bearing axial end play to ensure low vibration or noise levels.

DESCRIPTION OF PREFERRED EMBODIMENTS

The means providing the features and advantages of the present invention are illustrated in the accompanying drawings wherein:

FIG. 1 is a perspective view of a dental handpiece illustrating the relative locations of a high-speed gas-driven motor housing and a hand-grippable portion;

FIG. 2 is a side elevational view, partly in section, showing the position of the presently preferred turbine cartridge assembly of the present invention within the handpiece motor housing of FIG. 1;

FIG. 3 is a side elevational view, partly in section, of the turbine cartridge assembly of FIG. 2;

FIG. 4 is a side sectional view of a second embodiment of a turbine cartridge assembly of this invention;

Figure 5:
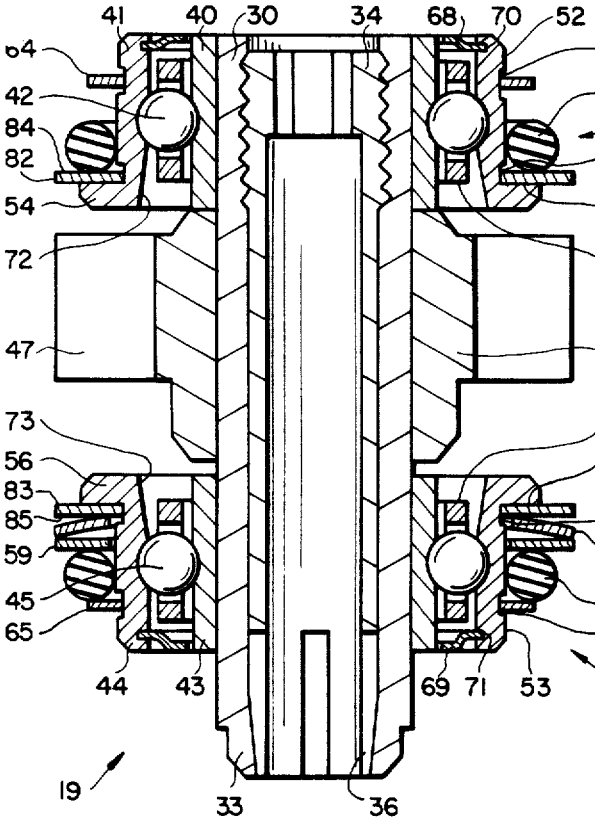
FIG. 5 is a side sectional view of a third embodiment of a turbine cartridge assembly of this invention.

Illustrated in FIG. 1 is a dental handpiece 10 including a barrel-shaped handle portion 11 having an outer wall 12 with flutes 13 which provide a hand-grippable surface. Handle portion 11 has at one end thereof an elongated neck 14 joined to handle portion 11 at a knuckle 15. Neck 14 terminates in head 16 having a gas-driven motor 17 provided by a motor housing 18 and turbine cartridge assembly 19, as depicted in FIG. 2. Motor housing 18 is defined by a substantially cylindrical inner side wall 20, having an axis lying generally transverse to the axis of neck 14, and by a pair of oppositely disposed end walls transverse to side walls 20. One housing end wall 21 is integrally formed with housing side wall 20 within head 16. The other housing end wall is furnished by end cap 22 which has an annular-shaped flange 23 extending into housing 18 in a generally axial direction. Flange 23 has an exteriorly threaded portion 24 which engages an interiorly threaded portion 25 on an adjacent portion of side wall 20. End cap 22 contains an orifice 26 which, when end cap 22 is threadedly secured to housing side wall 20, is axially aligned with an orifice 27 in oppositely disposed end wall 21.

Integrally formed along a portion of housing side wall 20 near end wall 21 is an annular-shaped ledge or shoulder 28 which extends radially inwardly toward the axis of housing 18. Shoulder 28 comprises a part of end wall 21 and provides a portion of the means for supporting turbine cartridge assembly 19 within housing 18. At the opposite end of housing 18, annular flange 23 of end cap 22 provides an annular-shaped shoulder 29 which also comprises a portion of the means for supporting turbine cartridge assembly 19 within housing 18.

Turbine cartridge assembly 19 comprises an elongated rotor shaft 30 having an axis of rotation that is substantially coincident with the axis of motor housing 18. Rotor shaft 30 has an axial bore 31 extending the length thereof. There is an interiorly threaded portion 32 at the end of rotor shaft 30 adjacent end cap 22. At its opposite end, rotor shaft 30 has a tapered portion 33 which slopes inwardly toward the axis of rotor shaft 30. Contained within rotor shaft bore 31 is a collet 34 having at one end an exteriorly threaded portion 35 which engages threaded portion 32 of rotor shaft 30. At its opposite end, collet 34 has a plurality of jaws 36 for gripping a shank 37 of a work tool when collet 34 is threaded into rotor shaft 30. Additional details and advantages of construction of a dental handpiece having the illustrated collet may be found in U.S. Pat. No. 3,120,706 to Turchi et al, the disclosure of which is incorporated herein by reference. A description of means for inserting and removing a work tool, such as a dental bur, into and from collet 34 may be found in U.S. Pat. No. 3,947,966 to Lieb at al.

Rotor shaft 30 is journalled upon a pair of first and second bearing assemblies 38 and 39, respectively, which are in axially spaced relationship along rotor shaft 30. It should be noted that the terms "first" and "second" designating bearing assemblies 38 and 39 are for convenience of discussion only, and that either bearing assembly could be designated "first" or "second" since the designation is entirely arbitrary. Hence, the following description relating to the "first bearing assembly" may, as well, relate to the "second bearing assembly", and vice versa.

First bearing assembly 38 comprises a ring-like inner race 40, which is fixedly journalled upon a portion of rotor shaft 30 adjacent end cap 22, and a ring-like outer race 41 spaced therefrom. Inner race 40 and outer race 41 provide a bearing housing in which a plurality of movable ball bearing elements 42 can be confined between and frictionally engaged with races 40 and 41. Second bearing assembly 39 similarly comprises an inner race 43, an outer race 44 and movable ball bearing elements 45 confined and frictionally engaged therebetween. Inner race 43 is fixedly journalled upon rotor shaft 30 in spaced relationship with inner race 40 of first bearing assembly 38, that is, inner race 43 of second bearing assembly 39 is journalled upon a portion of rotor shaft 30 closer to end wall 21. Alternatively, inner races 40 and 43 could as well be integrally formed with rotor shaft 30.

Rotor 46 including a plurality of vanes 47 radiating outwardly from rotor shaft 30 is fixedly journalled upon rotor shaft 30 between first and second bearing assemblies 38 and 39. Vanes 47 impart rotational movement to rotor shaft 30 when a high velocity gas stream impinges upon vanes 47, as is well known in the art. A suitable high velocity gas stream may be provided from an external source of compressed air (not shown) connected to passageway 48 within handle portion 11, which passageway 48 is in communication with motor housing 18 by means of inlet port 49 in motor housing side wall 20. An exhaust port 50 in another portion of side wall 20 spaced from inlet port 49 provides communication between motor housing 18 and exhaust passageway 51. Exhaust air flows from the motor housing via port 50 and the hollow portions of handpiece 10 within neck 14 and handle portion 11 during use of the handpiece.

Outer races 41 and 44 of first and second bearing assemblies 38 and 39, respectively, each have substantially cylindrically shaped outer walls 52 and 53 facing in a direction radially outwardly of the axis of rotor shaft 30. When turbine cartridge assembly 19 is positioned within motor housing 18, the face of each of convex outer walls 52 and 53 is substantially concentric with the portions of cylindrically-shaped concave housing side wall 20 adjacent thereto. Outer wall 52 of first bearing assembly outer race 41 has a flange 54 integrally formed as the edge portion thereof closer to second bearing assembly 39. Flange 54 extends radially outwardly from the face of outer wall 52 with respect to the axis of rotor shaft 30. Preferably, flange 54 extends circumferentially about outer wall 52 to provide an annular ledge or shoulder 55. Similarly, outer wall 53 of second bearing assembly outer race 44 has a flange 56 integrally formed as the edge portion thereof closer to first bearing assembly 38. Flange 56 extends radially outwardly from the face of outer wall 53 with respect to the axis of rotor shaft 30. Flange 56 preferably extends circumferentially about outer wall 53 to provide an annular ledge or shoulder 57.

Adjacent flange shoulder 55 of first bearing assembly 38 is a flat washer 58 having an annular or ring-like shape, which washer 58 lies circumferentially about outer wall 52. The inner diameter of washer 58 is less than the outer diameter of flange shoulder 55, as measured in a plane substantially perpendicular to the axis of rotor shaft 30, while the outer diameter of washer 58 is greater than the outer diameter of flange shoulder 55. A ring-like flat washer 59 of construction similar to washer 58 lies circumferentially about outer wall 53 near flange shoulder 57 of second bearing assembly 39.

Flat washers 58 and 59 provide rigid support means for supporting turbine cartridge assembly 19 upon annular-shaped shoulders 29 and 28, respectively, located on end cap 22 and side wall 20 of motor housing 18, when turbine cartridge assembly 19 is operably positioned within housing 18. Each of flat washers 58 and 59 tends to prevent movement of outer races 41 and 44, respectively, in opposite directions away from rotor vanes 47 along the axis of rotor shaft 30.

Figure 6:
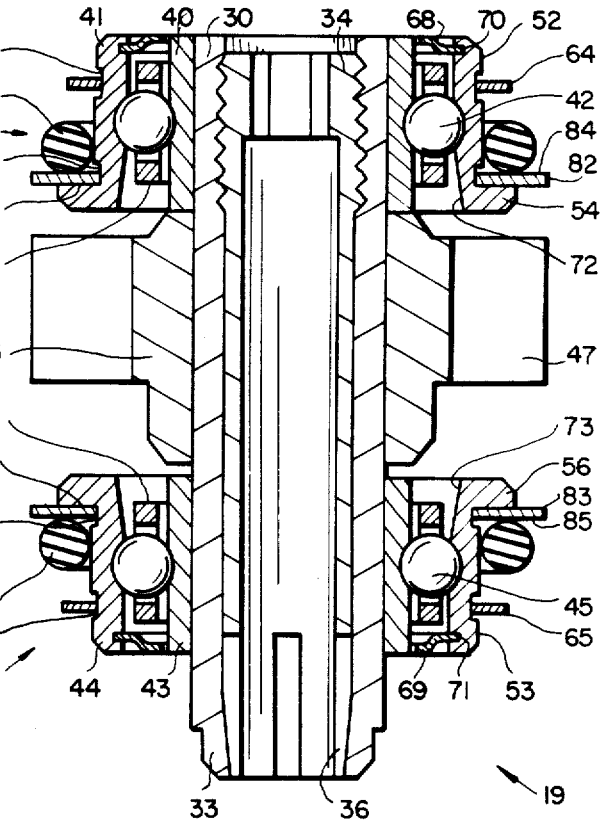
FIG. 6 is a side sectional view of a fourth embodiment of a turbine cartridge assembly of this invention.

The rigid axial support means may be provided by other constructions in addition to those described above. For example, as shown in FIG. 6, grooves 80 and 81 each run circumferentially about outer walls 52 and 53, respectively, with each of the grooves lying in a plane substantially perpendicular to the axis of rotor shaft 30. Within each of grooves 80 and 81 is a snap ring 82 and 83, respectively, retained within the grooves, and in rigid connection with the respective outer races, by the spring bias of the snap ring. Snap rings 82 and 83 provide shoulders 84 and 85, respectively, extending radially outwardly of outer race outer walls 52 and 53, respectively. Shoulders 84 and 85 each have an outer diameter in the radial direction sufficient to provide rigid axial support for the turbine cartridge assembly upon annular shoulders 29 and 28, respectively.

Figure 7:
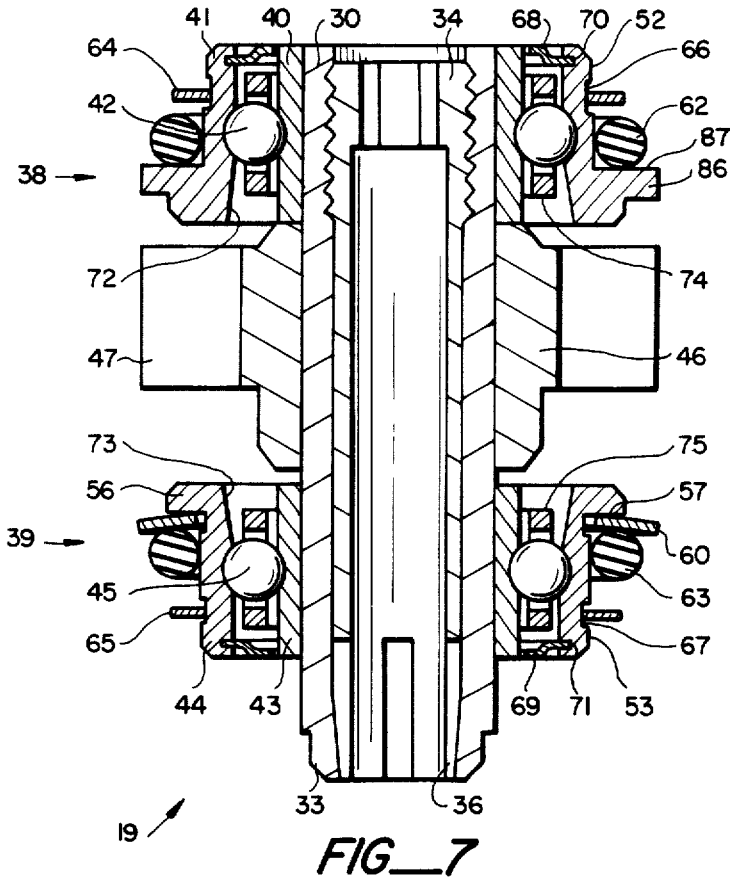
FIG. 7 is a side sectional view of a fifth embodiment of a turbine cartridge assembly of this invention.

Another variation of the rigid axial support means is depicted in FIG. 7. Integrally formed with bearing assembly outer race 41 is a flange 86 which has an outer diameter in the radial direction sufficient to define a shoulder 87 which provides axial support for turbine cartridge assembly 19 upon end wall shoulder 29 of motor housing 18. Flange 86 thus provides rigid axial support like the combination of flange 55 and flat washer 58 depicted in FIG. 3, for example.

As depicted in FIG. 2, there is provided in association with second bearing assembly 39 a resilient spacer member comprising a wavey spring washer 60 interposed between flange shoulder 57 and flat washer 59. Spring washer 60 has a substantially sinuous configuration and thus provides a spring-like thrust tending to urge outer race 44 toward outer race 41 in an axial direction. With turbine cartridge assembly 19 operably positioned within housing 18, flat washer 59 of second bearing assembly 39 is supported by shoulder 28 located on a portion of housing side wall 20. A reaction force from shoulder 28 through flat washer 59 opposes the spring compression force of spring washer 60.

Likewise, other embodiments of the turbine cartridge assembly of the invention may have a spring washer 60 associated with second bearing assembly 39. As shown in FIG. 5 spring washer 60 is interposed between shoulder 85 of snap ring 83 and flat washer 59. In the turbine cartridge assembly of FIG. 7, spring washer 60 may be interposed between flange shoulder 57 and end wall shoulder 28 when the turbine cartridge assembly is operably positioned within motor housing 18. In each of these constructions, a reaction force is transmitted between a portion of housing end wall 21 and second bearing assembly outer race 44.

Total axial loading of first and second bearing assemblies 38 and 39 may be accomplished with a single wavey washer 60 positioned in association with second bearing assembly 39 as depicted in FIGS. 2, 5 and 7. The illustration of transmitted forces within turbine cartridge assembly 19, as indicated by the arrows in FIG. 2, demonstrates the manner in which axial preloading of both bearing assemblies of turbine cartridge assembly 19 may be accomplished by a single spring washer 60. The pre-load compression force exerted by wavey washer 60 is transmitted through outer race 44 of second bearing assembly 39 to ball bearing element 45 then to inner race 43 affixed to one end of rotor shaft 30. At the other end of rigid rotor shaft 30, the pre-load force is transmitted from the rotor shaft through inner race 40 of the first bearing assembly to ball bearing element 42 and then to outer race 41 which is restrained from axial displacement away from rotor vanes 47 by flat washer 58 supported upon annular shoulder 29 of end cap 22. Axial pre-loading is likewise achieved by a single spring washer 60 in the turbine cartridge assemblies of FIGS. 5 and 7.

In another embodiment of the turbine cartridge assembly as depicted in FIG. 4, resilient spacer members comprising wavey spring washers 61 and 60, respectively, are associated with each of first and second bearing assemblies 38 and 39. Each of wavey washers 60 and 61 has a sinuous configuration and provides a spring-like thrust tending to urge outer races 41 and 44 toward each other in the axial direction. The two spring washers 60 and 61 thus cooperate to provide a total pre-loading of the first and second bearing assemblies.

Typically, a suitable spring washer is fabricated of materials such as spring steel or phosphor bronze and will have dimensions and a spring constant adapted to the particular configuration and desired degree of axial play of the bearing assemblies of a turbine cartridge assembly. It is preferred that in either embodiment illustrated in FIG. 2 and FIG. 3 the total axial pre-loading of the first and second bearing assemblies, as provided by one or more wavey washers, should be in the range of about 0.5 to about 1.5 pounds, which provides a good balance between low noise and vibration characteristics and long bearing life.

Although the described axial pre-loading means may be used successfully in a turbine cartridge assembly designed to have bearing assemblies which are in direct frictional contact with a motor housing side or end walls, it is preferred that resilient spacer rings be interposed between the bearing assemblies and adjacent portions of housing side wall 20 to provide radial support and a compliant mounting or suspension for turbine cartridge assembly 19. As illustrated in FIG. 2, a pair of resilient rings 62 and 63, such as commercially available O-rings fabricated of rubbery material, lie circumferentially about outer walls 52 and 53 of the outer races of first and second bearing assemblies 38 and 39, respectively. Preferably, each of O-rings 62 and 63 has an inner diameter in the radial direction with respect to the axis of rotor shaft 30 which is slightly less than the outer diameter of outer walls 52 and 53 so that each of O-rings 62 and 63 is in a slightly stretched configuration around its respective outer race. Each of resilient O-rings 62 and 63 will have an outer diameter slightly greater than the diameter of the housing at the portion of the housing side wall adjacent to the O-ring. Thus when turbine cartridge assembly 19 is positioned within housing 18, O-rings 62 and 63 become compressed in the radial direction. This radial compression of the O-rings provides both a sleeve or frictional fit and suitable alignment of turbine cartridge assembly 19 within housing 18. In addition to inhibiting radial displacement of the turbine cartridge assembly, the O-rings inhibit transfer of vibration from the cartridge assembly to the handle portion during use of the handpiece.

The O-rings 62 and 63 may be fabricated of practically any elastic or resilient material that has good vibration and noise damping properties and which resists high temperature and steam conditions typical of repeated autoclave cycles required for sterilization during the useful life of the dental instrument. Satisfactory materials include, for example, neoprene elastomer, ethylenepropylene elastomer, fluorocarbon elastomer and butadiene/acrylonitrile elastomer (known commercially as Buna-N rubber).

A significant advantage of a turbine cartridge assembly of this invention is provided by the ease of removal and replaceability of the turbine cartridge assembly from and to a dental handpiece, which is attributable to the feature of all of the components of the turbine cartridge assembly being removed or replaced as a unitary assembly. The aforementioned one or more spring washers for effecting proper bearing pre-loading and the resilient O-rings which provide vibration and noise damping are all retained on the turbine cartridge assembly, thereby precluding removal or reinsertion of these parts separately from other turbine components.

Retention of the spring washers or the O-rings on the turbine cartridge assembly may be accomplished by cooperation of bearing outer race flanges 54 and 56 with various means associated with the outer race of each bearing assembly. For example, in some constructions each of O-rings 62 and 63 may have a sufficiently secure friction fitting with the respective outer wall of first and second bearing assembly outer races 41 and 44 to prevent axial movement of one or more spring washers toward the ends of rotor shaft 30. More likely, each of first and second bearing assemblies 38 and 39 will have additional retaining means for keeping both the one or more spring washers and the O-rings on turbine cartridge assembly 19 as shown, for example, in each of the embodiments of FIGS. 2, 3 and 4. The retaining means comprise snap rings 64 and 65 which rest in grooves 66 and 67 running circumferentially about outer walls 52 and 53 of first and second bearing assembly outer races 41 and 44, respectively. Snap rings 64 and 65 retain flat washers 58 and 59, spring washer 60 (and 61 of the embodiment of FIG. 4) and O-rings 62 and 63 upon their respective bearing assemblies, so that none of these components become lost or misaligned during removal or replacement of the turbine cartridge assembly from the motor housing.

As another aspect of the invention, a turbine cartridge assembly may lack the aforementioned bearing axial pre-load means as provided, for example, by one or more spring washers interposed between one or more of the bearing assemblies and adjacent portions of the housing end walls. For example, as shown in FIG. 6, each of first and second bearing assemblies 38 and 39, respectively, has rigid axial support means which provide support for turbine cartridge assembly 19 upon end wall shoulders 29 and 28, respectively, when turbine cartridge assembly 19 is operably positioned within motor housing 18. The rigid support means is depicted as comprising snap rings 82 and 83 rigidly connected to bearing assembly outer races 41 and 43 by the spring tension of each of snap rings 82 and 83, respectively, within each of grooves 80 and 81. It should be understood, however, that any of the other described rigid axial support means of FIGS. 2, 3, 4, 5 and 7, or combinations thereof, could be utilized as well. Turbine cartridge assembly 19 of FIG. 6 is characterized as compliantly mountable, though lacking axial pre-loading means, inasmuch as there is provided radial support means which comprise resilient O-rings 62 and 63.

Each of bearing assemblies 38 and 39 may also contain shield rings 68 and 69 resting in grooves 70 and 71, respectively, running circumferentially about inner walls 72 and 73 of first and second bearing assembly outer races 41 and 44, respectively. The purpose of shield rings 68 and 69 is to aid in retention of lubricant within and around each of ball bearing retainers 74 and 75 and to retard contamination of the bearings by entry of particulate matter into the bearing cages.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental handpiece comprising a gas-driven motor, said motor including a housing and a turbine cartridge assembly within said housing, said housing defined by a substantially cylindrical side wall and by a pair of oppositely disposed end walls transverse to said side wall, said housing having turbine cartridge assembly support means located on portions of said walls for supporting said turbine cartridge assembly, said turbine cartridge assembly removably positionable as a unitary assembly within said housing, said turbine cartridge assembly comprising:

a rotor shaft having a plurality of vanes thereon, said rotor shaft having an axis of rotation substantially coincident with the axis of said substantially cylindrical side wall of said housing;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means providing radial support for said turbine cartridge assembly upon said substantially cylindrical side wall of said housing;

rigid axial support means connected to said outer race of said first bearing assembly for axially supporting said first bearing assembly outer race upon said turbine cartridge support means of said housing;

bearing pre-load means comprising flexible axial support means associated with said outer race of said second bearing assembly for yieldingly supporting said outer race upon said turbine cartridge support means of said housing;

first retaining means for retaining said radial support means upon said outer race of said first bearing assembly, said first retaining means preventing movement of said radial support means in an axial direction away from said rotor shaft vanes; and second retaining means for retaining said radial support means and said flexible axial support means upon said outer race of said second bearing assembly, said second retaining means preventing movement of said radial support means and said flexible support means in an axial direction away from said rotor shaft vanes;

whereby said rigid axial support means and said flexible axial support means coact with turbine cartridge support means of said housing to provide axial pre-loading of said first and second bearing assemblies when said turbine cartridge assembly is operatively positioned within said housing.

2. The dental handpiece of claim 1 wherein said radial support means comprises an outer wall on each of said bearing assembly outer races, said outer wall facing radially outwardly of the axis of said rotor shaft; and a ring of resilient material frictionally engaged about a circumferential portion of said outer race outer wall of each of said bearing assemblies, said ring having an outer diameter sufficient to provide a compression fit between said outer race outer wall and a portion of said housing side wall when said turbine cartridge assembly is operably positioned within said housing.

3. The dental handpiece of claim 2 wherein said ring of resilient material is an O-ring fabricated of a material selected from the group consisting of neoprene elastomer, fluorocarbon elastomer, ethylene propylene elastomer and butadiene/acrylonitrile elastomer.

4. The dental handpiece of claim 1 wherein said rigid axial support means comprises a flange connected to said outer race of said first bearing assembly, said flange having an outer diameter in the radial direction sufficient to provide axial support for said turbine cartridge assembly upon a portion of said housing end wall adjacent said first bearing assembly.

5. The dental handpiece of claim 1 wherein said rigid axial support means comprises:

a flange connected to said outer race of said first bearing assembly, said flange extending radially outwardly from said outer race; and a substantially flat washer interposed between said flange on said first bearing assembly outer race and said turbine cartridge support means of said housing, said flat washer having an inner diameter smaller than the outer diameter of said radially extending flange, and having an outer diameter of sufficient dimension so that said flat washer supports said outer race upon turbine cartridge assembly support means located on an end wall portion of said housing adjacent said first bearing assembly.

6. The dental handpiece of claim 1 wherein said rigid axial support means comprises an outer wall on said first bearing assembly outer race, said outer wall facing radially outwardly of the axis of said rotor shaft;

a groove running circumferentially about said outer race outer wall, said groove lying in a plane substantially perpendicular to the axis of said rotor shaft;

a spring-like snap ring retained within said groove, said snap ring forming a shoulder extending radially outwardly of said outer race outer wall, said shoulder having an outer diameter in the radial direction sufficient to provide rigid axial support for said turbine cartridge assembly upon one of said end walls of said housing.

7. The dental handpiece of claim 1 wherein said flexible axial support means comprises a flange connected to said outer race of said second bearing assembly, said flange extending radially outwardly from said outer race, and a resilient spacer member interposed between said flange on said second bearing assembly outer race and a portion of said housing end wall adjacent said second bearing assembly, said spacer member having spring-like resilience adapted to transmit a controlled compression force between said second bearing assembly outer race and said housing end wall.

8. The dental handpiece of claim 7 wherein said resilient spacer member is a ring-like spring washer.

9. The dental handpiece of claim 8 wherein said ring-like spring washer has a spring constant sufficient to provide a pre-load to each of said bearing assemblies in the range of about 0.5 to about 1.5 pounds when said turbine cartridge assembly is operably positioned within said housing.

10. The dental handpiece of claim 1 wherein each of said first and second retaining means comprises:

an outer wall on each of said bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said groove by the spring bias of each of said snap rings, each of said snap rings forming an annular-shaped collar extending radially outwardly of each of said outer race outer walls, each of said collars having an outer diameter in the radial direction sufficient to retard movement of said radial support means or said flexible support means, or both, in an axial direction away from said rotor shaft vanes.

11. The dental handpiece of claim 1 further including a bore within said rotor shaft, said bore having an axis substantially coincident with the axis of said rotor shaft, said rotor shaft having a threaded portion along a wall portion of said bore, and a collet having adjustable jaws for gripping a work tool, said collet having a threaded portion on an outer wall portion thereof for threadably engaging said threaded portion of said rotor shaft.

12. A turbine cartridge assembly removably positionable within a housing of a gas-driven motor of a dental handpiece wherein the housing is defined by a substantially cylindrical side wall and by a pair of oppositely disposed end walls transverse to said side wall, and includes turbine cartridge assembly support means located on portions of the end walls of the housing; said turbine cartridge assembly comprising:

a rotor shaft having a plurality of vanes thereon, said rotor shaft defining an axis of rotation;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means providing radial support for said turbine cartridge assembly when in contact with the substantially cylindrical side wall of the housing, when said turbine cartridge assembly is operatively positioned within the housing of the handpiece;

means for yieldingly coacting with the turbine cartridge assembly support means of the housing of the handpiece for axially pre-loading said first and said second bearing assemblies when said turbine cartridge assembly is operably positioned within the housing, said means for yieldingly coacting with said turbine cartridge support means comprising a ring-like spring washer retained about the outer race of at least one of said first and second bearing assemblies, said spring washer having a spring constant sufficient to provide a static preload to said bearing assemblies in the range of about 0.5 to about 1.5 pounds, when said turbine cartridge assembly is operably positioned within a handpiece housing with the spring washer interposed between said bearing assembly outer race and the turbine cartridge support means of the housing, said turbine cartridge assembly being adapted for placement in, and removal from, the housing as a unitary assembly.

13. The turbine cartridge assembly of claim 12 wherein said radial support means comprises an outer wall on each of said bearing assembly outer races, each of said outer walls facing radially outwardly of the axis of said rotor shaft; and a ring of resilient material frictionally engaged about a circumferential portion of each of said outer race outer walls of each of said bearing assemblies, each of said rings having an outer diameter sufficient to provide a compression fit between each of said outer race outer walls and an adjacent portion of a handpiece housing side wall when said turbine cartridge assembly is operably positioned within the housing.

14. The turbine cartridge assembly of claim 13 wherein said ring of resilient material is an O-ring fabricated of a material selected from the group consisting of neoprene elastomer, fluorocarbon elastomer, ethylene-propylene elastomer and butadiene/acrylonitrile elastomer.

15. The turbine cartridge assembly of claim 12 further including rigid axial support means comprising a flange connected to said outer race of said first bearing assembly, said flange having an outer diameter in the radial direction sufficient to provide axial support for said turbine cartridge assembly upon a portion of a handpiece housing end wall when said turbine cartridge assembly is removably positioned within a handpiece housing.

16. The turbine cartridge assembly of claim 12 further including rigid axial support means comprising:

a flange connected to said outer race of said first bearing assembly, said flange extending radially outwardly from said outer race; and a substantially flat washer between said flange of said first bearing assembly outer race and said radial support means, said flat washer having an inner diameter smaller that the outer diameter of said radially extending flange, and having an outer diameter of sufficient dimension so that said flat washer supports said outer race upon turbine cartridge assembly support means of a handpiece housing when said turbine cartridge assembly is operably positioned within the housing.

17. The turbine cartridge assembly of claim 12 further including rigid axial support means comprising:

an outer wall on each of said bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves, each of said snap rings forming a shoulder extending radially outwardly of each of said outer race outer walls, each of said shoulders having an outer diameter in the radial direction sufficient to provide axial support for said turbine cartridge assembly upon an adjacent end wall of a handpiece housing.

18. A turbine cartridge assembly removably positionable within a housing of a gas-driven motor of a dental handpiece wherein the housing is defined by a substantially cylindrical side wall and by a pair of oppositely disposed end walls transverse to said wall, and includes turbine cartridge assembly support means located on portions of said end walls of said housing; said turbine cartridge assembly comprising:

a rotor shaft having a plurality of vanes thereon, said rotor shaft defining an axis of rotation;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means providing radial support for said turbine cartridge assembly when in contact with the substantially cylindrical side wall of a handpiece housing;

bearing pre-load means associated with at least one of said bearing assembly outer races for yieldingly coacting with the turbine cartridge assembly support means in the housing of the handpiece for axially pre-loading said first and said second bearing assemblies when said turbine cartridge assembly is operably positioned within the housing, said turbine cartridge assembly being adapted for placement in, and removal from, the housing as a unitary assembly;

retaining means mounted on each of said bearing assembly outer races for preventing movement of said radial support means or said means for yieldingly coacting with the housing turbine cartridge assembly support means or both in an axial direction away from said rotor shaft vanes.

19. The turbine cartridge assembly of claim 18 wherein said radial support means comprises an outer wall on each of said bearing assembly outer races, each of said outer walls facing radially outwardly of the axis of said rotor shaft; and a ring of resilient material frictionally engaged about a circumferential portion of each of said outer race walls of each of said first and second bearing assemblies, each of said rings having an outer diameter sufficient to provide a compression fit between each of said outer race outer walls and an adjacent portion of a handpiece housing side wall when said turbine cartridge assembly is operably positioned within the housing.

20. The turbine cartridge assembly of claim 19 wherein said ring of resilient material is an O-ring fabricated of a material selected from the group consisting of neoprene elastomer, fluorocarbon elastomer, ethylene-propylene elastomer and butadiene/acrylonitrile elastomer.

21. The turbine cartridge assembly of claim 18 further including rigid axial support means comprising a flange connected to said outer race of said first bearing assembly, said flange having an outer diameter in the radial direction sufficient to provide axial support for said turbine cartridge assembly upon a portion of a handpiece housing end wall when said turbine cartridge assembly is removably positioned within a handpiece housing.

22. The turbine cartridge assembly of claim 18 further including a rigid axial support means comprising:

a flange connected to said outer race of said first bearing assembly, said flange extending radially outwardly from said outer race; and a substantially flat washer between said flange on said first bearing assembly outer race and said radial support means, said flat washer having an inner diameter smaller that the outer diameter of said radially extending flange, and having an outer diameter of sufficient dimension so that said flat washer supports said outer race upon turbine cartridge assembly support means of a handpiece housing when said turbine cartridge assembly is operably positioned within the housing.

23. The turbine cartridge assembly of claim 18 further including rigid axial support means comprising:

an outer wall on each of said first and second bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves, each of said snap rings forming a shoulder extending radially outwardly of each of said outer race outer walls, each of shoulders having an outer diameter in the radial direction sufficient to provide axial support for said turbine cartridge assembly upon an adjacent end wall of a handpiece housing when said turbine cartridge assembly is operably positioned within the housing.

24. The turbine cartridge assembly of claim 18 wherein said means for yieldingly coacting with turbine cartridge support means of a handpiece housing comprises a resilient spacer member retained about said outer race of at least one of said first and second bearing assemblies, said spacer member adapted to transmit a controlled compression force between said outer race and the turbine cartridge assembly support means of the housing, so as to urge said outer race in a axial direction, toward said rotor vanes.

25. The turbine cartridge assembly of claim 24 wherein said resilient spacer member is a ring-like spring washer.

26. The turbine cartridge assembly of claim 25 wherein said ring-like spring washer has a spring constant sufficient to provide a static pre-load to said bearing assemblies in the range of about 0.5 to about 1.5 pounds, when said turbine cartridge assembly is operably positioned within a handpiece housing with the spring washer interposed between said bearing assembly outer race and turbine cartridge support means of the housing.

27. The turbine cartridge assembly of claim 18 wherein said means for yieldingly coacting with turbine cartridge support means of a handpiece housing comprises:

a first resilient spacer and member retained about said outer race of said first bearing assembly, said first spacer member adapted to transmit a controlled compression force between said outer race of said first bearing assembly and an adjacent portion of the turbine cartridge assembly support means of the housing;

a second resilient spacer member retained about said outer race of said second bearing assembly said second spacer member adapted to transmit a controlled compression force between said outer race of said second bearing assembly and an adjacent portion of the turbine cartridge assembly support means of the housing;

wherein said first and second spacer members cooperate with the turbine cartridge support means of the housing to provide axial pre-loading of said first and second bearing assemblies.

28. The turbine cartridge assembly of claim 27 wherein each of said resilient spacer member is a ring-like spring washer.

29. The turbine cartridge assembly of claim 28 wherein said ring-like spring washers have spring constants sufficient to provide a static pre-load to said bearing assemblies in the range of about 0.5 to about 1.5 pounds, when said turbine cartridge assembly is operably positioned within a handpiece housing with said spring washer interposed between said bearing assembly outer races and the turbine cartridge support means of the housing.

30. The turbine cartridge assembly of claim 18 wherein said retaining means comprises:

an outer wall on each of said first and second bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves by the spring bias of each of said snap rings, each of said snap rings forming an annular-shaped collar extending radially outwardly of each of said outer race outer walls, each of said collars having an outer diameter in the radial direction sufficient to retard movement of said radial support means and said flexible support means in an axial direction away from said rotor shaft vanes.

31. A dental handpiece comprising a gas-driven motor, said motor including a housing and a turbine cartridge assembly within said housing, said housing defined by a substantially cylindrical side wall and by a pair of oppositely disposed end walls transverse to said side wall, said housing having turbine cartridge assembly support means located on portions of said end walls for supporting said turbine cartridge assembly, said turbine cartridge assembly removably positionable as a unitary assembly within said housing, said turbine cartridge assembly comprising:

a rotor shaft having a plurality of vanes thereon, said rotor shaft having an axis of rotation substantially coincident with the axis of said substantially cylindrical side wall of said housing;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means comprising a resilient member interposed between each of said bearing assemblies and an adjacent portion of said housing side wall for providing radial support for said turbine cartridge assembly when in contact with said substantially cylindrical side wall of said housing;

rigid axial support means connected to each of said outer races of said first and second bearing assemblies for axially supporting said outer races upon said turbine cartridge support means of said housing; and retaining means associated with each of said bearing assembly outer races for retaining said radial support means upon said turbine cartridge assembly and preventing movement of said radial support means in an axial direction away from said rotor shaft vanes during removal, or insertion, of said turbine cartridge assembly from, or in, said motor housing.

32. The dental handpiece of claim 31 wherein said radial support means comprises an outer wall on each of said first and second bearing assembly outer races, each of said outer walls facing radially outwardly of the axis of said rotor shaft; and each of said resilient members comprise a ring of resilient material frictionally engaged about a circumferential portion of each of said outer race outer walls of each of said first and second bearing assemblies, each of said rings having an outer diameter sufficient to provide a compression fit between each of said outer race outer walls and an adjacent portion of said housing side wall when said turbine cartridge assembly is operably positioned within said housing.

33. The dental handpiece of claim 32 wherein said ring of resilient material is an O-ring fabricated of a material selected from the group consisting of neoprene elastomer, fluorocarbon elastomer, ethylenepropylene elastomer and butadiene/acrylonitrile elastomer.

34. The dental handpiece of claim 31 wherein said rigid axial support means comprises a flange connected to each of said outer races of said first and second bearing assemblies, each of said flanges having an outer diameter in the radial direction sufficient to provide axial support for said turbine cartridge assembly upon a portion of said housing end wall.

35. The dental handpiece of claim 31 wherein said rigid axial support means comprises:

a flange connected to each of said outer races of said first and second bearing assemblies, each of said flanges extending radially outwardly from each of said outer races; and a substantially flat washer interposed between each of said flanges on each of said bearing assembly outer races and an adjacent portion of said turbine cartridge support means of said housing, each of said flat washers having an inner diameter smaller than the outer diameter of said radially extending flange adjacent to said washer, and having an outer diameter of sufficient dimension so that said flat washers support each of said outer races upon turbine cartridge assembly support means located on wall portions of the housing.

36. The dental handpiece of claim 31 wherein said rigid axial support means comprises an outer wall on each of said bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves, each of said snap rings forming a shoulder extending radially outwardly of each of said outer race outer walls, each of said shoulder having an outer diameter in the radial direction sufficient to provide axial support for said turbine cartridge assembly upon one of said end walls of said housing.

37. The dental handpiece of claim 31 wherein each of said retaining means comprises:

an outer wall of each of said bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves by the spring bias of each of said snap rings, each of said snap ring forming an annular-shaped collar extending radially outwardly of each of said outer race outer walls, each of said collars having an outer diameter in the radial direction sufficient to retard movement of said radial support means or said flexible support means, or both, in an axial direction away from said rotor shaft vanes.

38. A turbine cartridge assembly removably positionable within a housing of a gas-driven motor of a dental handpiece wherein the housing is defined by a substantially cylindrical side wall and by a pair of oppositely disposed end walls transverse to said wall, and includes turbine cartridge assembly support means located on portions of said end walls of said housing; said turbine cartridge assembly comprising:

a rotor shaft having a plurality of vanes thereon, said rotor shaft defining an axis of rotation;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means providing radial support for said turbine cartridge assembly when in contact with the substantially cylindrical side wall of a handpiece housing;

retaining means mounted on each of said bearing assembly outer races for preventing movement of said radial support means in an axial direction away from said rotor shaft vanes during removal, or insertion, of said turbine cartridge assembly from, or in, said motor housing.

39. The turbine cartridge assembly of claim 38 wherein said radial support means comprises an outer wall on each of said bearing assembly outer races, each of said outer walls facing radially outwardly of the axis of said rotor shaft; and a ring of resilient material frictionally engaged about a circumferential portion of each of said outer race outer walls of each of said first and second bearing assemblies, each of said rings having an outer diameter sufficient to provide a compression fit between each of said outer race outer walls and an adjacent portion of a handpiece housing side wall when said turbine cartridge assembly is operably positioned within the housing.

40. The turbine cartridge assembly of claim 39 wherein said ring of resilient material is an O-ring fabricated of a material selected from the group consisting of neoprene elastomer, fluorocarbon elastomer, ethylene-propylene elastomer and butadiene/acrylonitrile elastomer.

41. The turbine cartridge assembly of claim 38 further including rigid axial support means comprising a flange connected to each of said outer races of said first and second bearing assemblies, each of said flanges having an outer diameter in the radial direction sufficient to provide axial support for said turbine cartridge assembly upon portions of handpiece housing end walls when said turbine cartridge assembly is removably positioned within a handpiece housing.

42. The turbine cartridge assembly of claim 38 further including rigid axial support means comprising:

a flange connected to each of said outer race of said first and second bearing assemblies, each of said flanges extending radially outwardly from each of said outer races; and a substantially flat washer between each of said flanges of said first and second bearing assembly outer races and said associated radial support means, each of said flat washers having an inner diameter smaller that the outer diameter of said radially extending flange, and having an outer diameter of sufficient dimension so that each of said flat washers supports said outer race adjacent said flat washer upon turbine cartridge assembly support means of a handpiece housing when said turbine cartridge assembly is operably positioned within the housing.

43. The turbine cartridge assembly of claim 38 further including rigid axial support means comprising:

an outer wall on each of said bearing assembly outer races, each of said outer wall facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said groove by the spring bias of each of said snap rings, each of said snap rings forming a shoulder extending radially outwardly of each of said outer race outer walls, said shoulders having an outer diameter in the radial direction sufficient to provide axial support for said turbine cartridge assembly upon an adjacent end wall of a handpiece housing.

44. The turbine cartridge assembly of claim 38 wherein said retaining means comprises:

an outer wall on each of said bearing assembly outer races, each of said outer walls facing radially outwardly of the axis of said rotor shaft;

a groove running circumferentially about each of said outer race outer walls, each of said grooves lying in a plane substantially perpendicular to the axis of said rotor shaft;

a spring-like snap ring retained within each of said grooves by the spring bias of each of said snap rings, each of said snap rings forming an annular-shaped collar extending radially outwardly of each of said outer race outer walls, each of said collars having an outer diameter in the radial direction sufficient to retain said radial support means upon said turbine cartridge assembly.

45. A dental handpiece comprising a gas-driven motor, said motor including a housing and a turbine cartridge assembly within said housing, said housing defined by a substantially cylindrical side wall and by a pair of oppositely disposed end walls transverse to said side wall, said housing having turbine cartridge assembly support means located on portions of said end walls for supporting said turbine cartridge assembly, said turbine cartridge assembly removably positionable as a unitary assembly within said housing, said turbine cartridge assembly comprising:

a rotor shaft having a plurality of vanes thereon, said rotor shaft having an axis of rotation substantially coincident with the axis of said substantially cylindrical side wall of said housing;

a first bearing assembly comprising an inner race fixed to said rotor shaft, an outer race having an outer wall facing radially outwardly of the axis of said rotor shaft, and a plurality of movable bearing elements frictionally engaged with and confined between said inner race and said outer race;

a second bearing assembly comprising an inner race fixed to said rotor shaft, an outer race having an outer wall facing radially outwardly of the axis of said rotor shaft, and a plurality of movable bearing elements frictionally engaged with and confined between said inner race and said outer race of said second bearing assembly;

a flange connected to each of said outer race outer walls, said flange extending radially outwardly from said outer race;

a substantially flat washer interposed between said flange on said first bearing assembly outer race and said turbine cartridge support means of said housing, said flat washer having an inner diameter smaller than the outer diameter of said radially extending flange, and having an outer diameter of sufficient dimension so that said flat washer supports said outer race upon said turbine cartridge assembly support means of said housing;

a ring of resilient material frictionally engaged about a circumferential portion of said outer race outer wall of each of said bearing assemblies to provide radial support for said turbine cartridge assembly upon said motor housing side wall, said ring having an outer diameter sufficient to provide a compression fit between said outer race outer wall and a portion of said housing side wall;

a groove running circumferentially about said outer race outer wall of each of said bearing assemblies, said groove lying in a plane substantially perpendicular to the axis of said rotor shaft;

a spring-like snap ring retained within each of said grooves by the spring bias of said snap ring, said snap ring forming an annular-shaped collar extending radially outwardly of said outer race outer wall, each of said collars having an outer diameter in the radial direction sufficient to retain said flat washer and said ring of resilient material upon each of said turbine cartridge assembly outer race outer walls in cooperation, respectively, with said flange of each of said bearing assembly outer race outer walls; and a resilient spacer ring interposed between said flange and said flat washer of said second bearing assembly outer race, said spacer ring having a spring-like resilience adapted to transmit a controlled compression force between said outer race and a portion of said housing end wall adjacent said second bearing assembly so as to provide axial pre-loading of said first and second bearing assemblies within said motor housing.

46. The dental handpiece of claim 45 wherein said ring of resilient materials is an O-ring fabricated of a material selected from the group consisting of neoprene elastomer, fluorocarbon elastomer, ethylenepropylene elastomer and butadiene/acrylonitrile elastomer.

47. The dental handpiece of claim 45 wherein said resilient spacer ring is a spring washer.

48. The dental handpiece of claim 47 wherein said spring washer has a spring constant sufficient to provide a static pre-load to said bearing assemblies in the range of about 0.5 to about 1.5 pounds, when said turbine cartridge assembly is operably positioned within said housing.

49. The dental handpiece of claim 45 further comprising a resilient spacer ring interposed between said flange and said flat washer of said first bearing assembly outer race, said spacer ring having a spring-like resilience adapted to transmit a controlled compression force between said first bearing assembly outer race and a portion of said housing end wall adjacent said first bearing assembly so as to provide axial pre-loading of said first and second bearing assemblies within said motor housing in cooperation with said resilient spacer ring of said second bearing assembly.

50. The dental handpiece of claim 49 wherein each of said spacer rings of said first and second bearing assemblies is a spring washer.

51. The dental handpiece of claim 50 wherein said spring washers have spring constants sufficient to provide static pre-loading to said first and second bearing assemblies in the range of about 0.5 to about 1.5 pounds, when said turbine cartridge assembly is operably positioned within said housing.

52. A dental handpiece comprising a gas-driven motor, said motor including a housing and a turbine cartridge assembly within said housing, said housing defined by a substantially cylindrical side wall and by a pair of oppositely disposed end walls transverse to said side wall, said housing having turbine cartridge assembly support means located on portions of said walls for supporting said turbine cartridge assembly, said turbine cartridge assembly removably positionable as a unitary assembly within said housing, said turbine cartridge assembly comprising:

a rotor shaft having a plurality of vanes thereon, said rotor shaft having an axis of rotation substantially coincident with the axis of said substantially cylindrical side wall of said housing;

a first bearing assembly comprising an inner race fixed to said rotor shaft, an outer race, and a plurality of movable bearing elements frictionally engaged with and confined between said inner race and said outer race;

a second bearing assembly comprising an inner race fixed to said rotor shaft, an outer race, and a plurality of movable bearing elements frictionally engaged with and confined between said inner race and said outer race of said second bearing assembly;

radial support means associated with each of said first and second bearing assemblies, said radial support means providing radial support for said turbine cartridge assembly upon said substantially cylindrical side wall of said housing;

bearing pre-load means comprising flexible axial support means associated with each of said outer races of said first and second bearing assemblies for yieldingly supporting said outer races upon said turbine cartridge support means of said housing;

first retaining means for retaining said radial support means and said flexible axial support means upon said outer race of said first bearing assembly, said first retaining means preventing movement of said radial support means in an axial direction away from said rotor shaft vanes; and second retaining means for retaining said radial support means and said flexible axial support means upon said outer race of said second bearing assembly, said second retaining means preventing movement of said radial support means and said flexible support means in an axial direction away from said rotor shaft vanes;

whereby said flexible axial support means coact with turbine cartridge support means of said housing to provide axial pre-loading of said first and second bearing assemblies when said turbine cartridge assembly is operatively positioned within said housing.

*53. A self-contained cartridge assembly free of any outer enclosure for insertion and use as a unit in and for removal from a plurality of dental handpieces in which the housing interiors are different in size and in which each housing has a fluid inlet to direct fluid into the housing and an outlet to exhaust fluid from the housing and in which the housing becomes the enclosure for said cartridge assembly when said cartridge assembly is positioned therein, said cartridge assembly comprising sleeve shaped means of substantially the length of the housing and for engagement with a dental tool, a turbine having impeller faces extending into the housing and for impingement thereagainst by fluid directed into the housing through the fluid inlet thereof to rotate said turbine, said impeller being connected with said sleeve for conjoint rotation therewith, rollable bearings fixed on said sleeve on opposite sides of said impeller, and engaging means captured on said rollable bearings extending outward therefrom for fluid tight engagement with the wall of the handpiece housing on opposite ends of said impeller to confine and direct the inlet fluid against said impeller and the faces thereof to contain the fluid from flowing outward from between said cartridge and the engagement of said engaging means with the housing.*

*54. In a cartridge type turbine assembly as in claim 53, said engaging means being yieldable to cushion the engagement between said cartridge type turbine assembly and the housing to absorb vibrations therebetween.*

*55. In a cartridge type turbine assembly as in claim 54, said engaging means being of a size and being deformable to engage fluid tightly with housing walls of different sizes.*

*56. In a cartridge type turbine assembly as in claim 55, seat means on said rollable bearings mounting said engaging means to support the same in fixed position thereon and to prevent removal of said engaging means from their respective bearing.*

*57. In a cartridge type turbine assembly as in claim 55, said rollable bearings being spaced from and on opposite sides of said impeller faces from between 0.030 inches to 0.060 inches, and said impeller faces being spaced from the wall of the housing from between 0.010 inches and 0.030 inches.*

*58. In a cartridge type turbine assembly as in claim 53, said rollable bearings being spaced from and on opposite sides of said impeller faces from between 0.030 inches to 0.060 inches.*

*59. In a cartridge type turbine assembly as in claim 53, said impeller faces being spaced from the wall of the housing from between 0.010 inches and 0.030 inches.*

*60. In combination with a turbine operated dental handpiece having a housing with an interior wall to accommodate a turbine and fluid inlet and outlet means for the supply and exhaust respectively of fluid from the housing, a unitary turbine assembly free of any enclosure comprising rollable bearings relatively spaced from each other and each said bearing having inner and outer races, a rotatable turbine in said space between said bearings and having a plurality of impeller faces to receive the impingement of fluid thereagainst in the housing, seal means captured on the outer races of said bearings in fluid tight direct engagement with the interior wall of the housing to enclose said turbine between said spaced bearings and the interior wall such that fluid entering the housing is caused to impinge upon the impeller faces and to exhaust outward from the housing through the fluid outlet means, and an elongated dental tool holder mounting said bearings in their spaced relationship and with said turbine therebetween, said tool holder including a sleeve connected with said inner races of said bearings and with said turbine to rotate conjointly therewith, and said seal means being releasably engageable with the interior wall of the housing to enable said unitary turbine assembly to be inserted into and removed from engagement as a unit with the housing wall so that the housing becomes the enclosure for the unitary turbine assembly.*

*61. A unitary turbine assembly as in claim 60, said seal means being of a yieldable material and engaging with the interior walls of different sizes of housings fluid tightly to cause the outer race of its respective bearing to be non-rotatable relative to such engaged wall.*

*62. A unitary turbine assembly as in claim 60, said bearings being spaced from and on opposite sides of said rotatable turbine from between 0.030 inches to 0.060 inches.*

*63. A unitary turbine assembly as in claim 60, said impeller faces being spaced from the wall of the housing of the dental handpiece from between 0.010 inches to 0.030 inches.*

*64. A unitary turbine assembly as in claim 60, a recessed seat defined in the periphery of each of the outer races of said bearings, and said seal means on each of the outer races of said bearings being mounted within a respective one of said peripheral seats to retain the seal means fixed with respect to its respective bearing until forcefully removed therefrom for replacement.*

*65. A wall-less unitary cartridge type turbine assembly free of an outer enclosure for use in a circular housing of a dental handpiece in which the interior circular wall of the housing is utilized as the wall of the turbine assembly, said assembly comprising a rotatable axially elongated chuck having operable means for releasable engagement with a dental tool, a sleeve connected with said chuck for rotation therewith and rotation relative thereto to actuate with said operable means to releasably engage a dental tool, a turbine on said sleeve intermediate the ends thereof for rotation therewith, said turbine having a plurality of circumferentially spaced impeller faces against which fluid may impinge to rotate said turbine, rollable bearings spaced axially along said sleeve and on opposite sides of said impeller and axially from said impeller faces, each of said rollable bearings having inner and outer races with said inner race connected with said sleeve for rotation therewith and said outer race being rotatable with respect thereto, and seal means of yieldable deformable material mounted on said outer race of each of said bearings and from displacement therefrom so that said chuck, sleeve, turbine, rollable bearings and seal means are connected together as a unit free of an enclosing wall and for use as a cartridge type insert into and for removal from the housings of different dental handpieces with said seal means yielding to fit into the interior wall of the housing and deforming into fluid-tight engagement therewith such that the housing wall becomes the temporary enclosing wall of said turbine assembly while the same is therein and until said turbine assembly is removed from said housing by disengagement of said seal means therefrom.*

*66. A wall-less unitary cartridge type turbine assembly as in claim 65, said outer races of each of said rollable bearings having a circumferential seat defined in the outer periphery thereof in which said seal means is mounted and prevented from displacement.*

*67. A wall-less unitary cartridge type turbine assembly as in claim 65, said rollable bearings being spaced on opposite axial sides of said impeller faces from between 0.030 inches and 0.060 inches and said impeller faces being arranged on said unitary cartridge type turbine assembly such that when the same is within the housing said impeller faces are spaced from the interior wall thereof from between 0.010 inches and 0.030 inches.*

* * * * *